United States Patent
Bodenschatz et al.

(10) Patent No.: US 6,730,053 B1
(45) Date of Patent: May 4, 2004

(54) WRIST BANDAGE

(75) Inventors: Stefan Bodenschatz, Buxtehude (DE); Thorsten Stradt, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/233,832

(22) Filed: Jan. 20, 1999

(30) Foreign Application Priority Data

Jan. 23, 1998 (DE) .......................... 198 02 336

(51) Int. Cl.$^7$ ................................ A61F 13/00
(52) U.S. Cl. ................ 602/64; 602/20; 602/21; 602/62; 602/60; 602/61; 128/878; 128/879; 2/16; 2/20; 2/910; 2/917
(58) Field of Search ........................ 602/20, 21, 60–62, 602/64; 128/878, 879; 2/16, 20, 910, 917; D24/190

(56) References Cited

U.S. PATENT DOCUMENTS

| | | | |
|---|---|---|---|
| 3,327,703 A | | 6/1967 | Gamm ...................... 128/77 |
| 4,047,250 A | | 9/1977 | Norman ...................... 2/161 |
| 4,190,906 A | * | 3/1980 | Patton, Jr. .................... 2/162 |
| 4,716,892 A | * | 1/1988 | Brunswick ................... 602/21 |
| 5,421,811 A | * | 6/1995 | More et al. ............... 602/64 X |
| 5,513,657 A | * | 5/1996 | Nelson ................... 602/20 X |
| 5,649,900 A | * | 7/1997 | Kline ......................... 602/21 |
| 5,728,059 A | * | 3/1998 | Wiesemann .............. 602/21 X |
| 5,733,249 A | * | 3/1998 | Katzin ........................ 602/21 |
| 5,749,841 A | * | 5/1998 | Moore ........................ 602/21 |
| 6,267,743 B1 | * | 7/2001 | Bodenschatz et al. ........ 602/62 |
| 6,435,187 B1 | * | 8/2002 | Leithe et al. ............... 128/869 |

FOREIGN PATENT DOCUMENTS

| | | | |
|---|---|---|---|
| DE | 43 02 044 | | 3/1994 | ............ A61F/5/01 |
| DE | 196 51 912 | | 6/1998 | ............ A61F/13/00 |
| EP | 0 162 610 | | 11/1985 | ............ A61F/13/10 |
| EP | 162610 A1 | * | 11/1985 | .................. 602/21 |
| EP | 775476 | * | 5/1997 | .................. 602/21 |
| EP | 0 809 988 | | 12/1997 | ............ A61F/5/01 |
| EP | 0852935 A1 | * | 7/1998 | ................... 602/5 |
| EP | 0931529 A2 | * | 7/1999 | .................. 602/21 |
| FR | 2650176 | * | 2/1991 | .................. 602/21 |
| GB | 2307642 | | 6/1997 | ............ B25J/1/04 |
| WO | 92/19196 | | 11/1992 | ............ A61F/13/00 |

* cited by examiner

*Primary Examiner*—Nicholas D. Lucchesi
*Assistant Examiner*—L. Amerson
(74) *Attorney, Agent, or Firm*—Norris McLaughlin & Marcus

(57) ABSTRACT

Wrist bandage, consisting of an anatomically shaped section which receives the wrist and the hand and which is formed from a single piece of flexible and elastic material, the section narrowing in the proximal direction, the section having, on the medial edge, a cutout for receiving the thumb, and with at least two straps secured on the medial edge, which straps can be secured on the dorsal side of the bandage, and with a pocket which is secured on the palmar side of the bandage, in particular sewn thereon, in such a way that the centre axis of the pocket forms an inwardly directed arch.

7 Claims, 3 Drawing Sheets

WRIST BANDAGE

The invention relates to a wrist bandage for immobilizing the wrist.

BACKGROUND OF THE INVENTION

Depending on their design and on the indications for which they are intended, orthopaedic bandages exert a fixing, guiding, bracing and/or supporting action on the extremities of the human body.

These medical bandages must have a shape which corresponds to the anatomical circumstances in order to be able to act externally on the human body with a form fit and a force fit.

Medical bandages of this kind are produced by cutting out blanks from planar material, for example neoprene, knitted fabrics or woven fabrics. The anatomically appropriate shape is obtained via the shape of the blanks or darts, for example with gussets, and subsequent joining together of the blanks, as is also customary in articles of clothing.

This joining together can be done by sewing, gluing or other conventional methods. The great disadvantage of these bandages is that the exact anatomical fit can be achieved only with difficulty and there are a large number of connection points, for example seams. These connection points change the properties of the material used, and there is the danger of pressure points on the skin.

Dressings or bandages for the wrist are used in the treatment of distortions, contusions or sprains of the ulnar and radial ligaments. However, they can also support the healing process in the case of fissures of the metacarpal bones. Finally, by means of appropriate immobilization of the wrist, irritation of the metacarpal joints can be reduced to such a point that it entirely disappears.

EP 0 775 476 discloses a wrist bandage designed for both hands, using a flexible support material which has been anatomically shaped and on which two pockets are sewn, in each case in the lateral edge area, and these are used for receiving a splint. The bandage is applied and fixed around the wrist with the aid of several straps.

An advantage of the disclosed bandage is that it can be used for both hands. To do this, all that needs to be done is to remove the splint from one pocket and insert it into the other one.

However, a disadvantage of the bandage is that it is divided along the middle at least once, so that the bandage has to be sewn together from several pieces in order to guarantee a good fit on the wrist.

The pockets provided are sewn straight onto the support material, and this causes unattractive and undersired folds when the bandage is being applied.

SUMMARY OF THE INVENTION

The object of the invention is to make available a bandage which, by means of an explicit fit, ensures a reliable and stable fixation of the wrist at a very low production outlay and does not have the stated disadvantages of the prior art.

Accordingly, the invention provides a wrist bandage which consists of an anatomically shaped section which receives the wrist and the hand and which is formed from a single piece of flexible and elastic material, the section narrowing in the proximal direction, the section having, on the medial edge, a cutout for receiving the thumb, and with at least two straps secured on the medial edge, which straps can be secured on the dorsal side of the bandage.

A pocket is secured on the palmar side of the bandage, in particular sewn thereon, in such a way that the centre axis of the pocket forms an inwardly directed arch.

The pocket is in this case preferably situated in the edge area of the section, at least in the area of the cutout for receiving the thumb.

In an alternative embodiment, the wrist bandage likewise consists of an anatomically shaped section which receives the wrist and the hand and which is formed from a single piece of flexible and elastic material, the section narrowing in the proximal direction, the section having, on the medial edge, a cutout for receiving the thumb, and with at least two straps secured on the medial edge, which straps can be secured on the dorsal side of the bandage.

In contrast to the first variant, the pocket here is secured on the palmar side of the bandage, in particular sewn thereon, in such a way that the centre axis of the pocket has at least one inwardly directed kink.

Here too, the pocket is situated preferably in the edge area of the section, at least in the area of the cutout for receiving the thumb.

In a preferred embodiment, the centre axis of the pocket has a kink which encloses an angle of 150° to 170°.

The straps are preferably provided with a known VEL-CRO® closure (i.e. hook and loop fastener) which is secured on a roughened surface, the roughened surface being secured on the dorsal side of the bandage in such a way that the centre axis of the surface is located in an inwardly directed arch or the centre axis of the surface has at least one inwardly directed kink.

Here too, it has proven particularly advantageous if the centre axis has only one kink which encloses an angle of 150° to 170°.

The roughened surface is advantageously contiguous with the outer edge of the section.

It is moreover advantageous if one strap of the bandage is secured at the distal end of the medial edge, and the strap on the palmar side is provided with a padding.

The bandage consists in particular of a material which is flexible in the medial and lateral direction and substantially inflexible in the proximal and distal direction.

In addition to this, however, neoprene and similar materials have also proven suitable.

A substantially inflexible splint adapted to the anatomy of the inner surface of the hand can be inserted into the pocket of the bandage. The splint can be made of aluminium, for example.

In a further preferred embodiment of the bandage, the pocket secured on the palmar side of the bandage, in particular sewn thereon, has a roughened surface, and the roughened surface secured on the dorsal side of the bandage, in particular sewn thereon, is designed as a pocket. Thus, there are two preferably identical combinations of pocket/roughened surface present on the bandage. In this way, it is possible, with just a single design, to apply the bandage to either wrist, provided the splint has been inserted into the appropriate pocket.

The bandage according to the invention serves as a special post-traumatic and post-operative bandage for injuries in the wrist region.

A special bandage of this kind must have an explicit fit in order to ensure a reliable and stable fixation of the wrist.

In addition, a bandage according to the invention should be simple and inexpensive to produce and, unlike the situation in the prior art, it should not have to be joined together from a large number of cut-to-shape parts in order to achieve the necessary fit.

Surprisingly, it has been found that because the pocket, receiving the splint, and the roughened surface are not sewn straight onto the support material, as was previously the case, an excellent application of the bandage over the wrist is possible without forming folds.

A particularly advantageous embodiment of the bandage according to the invention will be described below with reference to a number of figures, but without thereby unnecessarily limiting the invention.

DETAILED DESCRIPTION OF THE INVENTION

Figure 1:
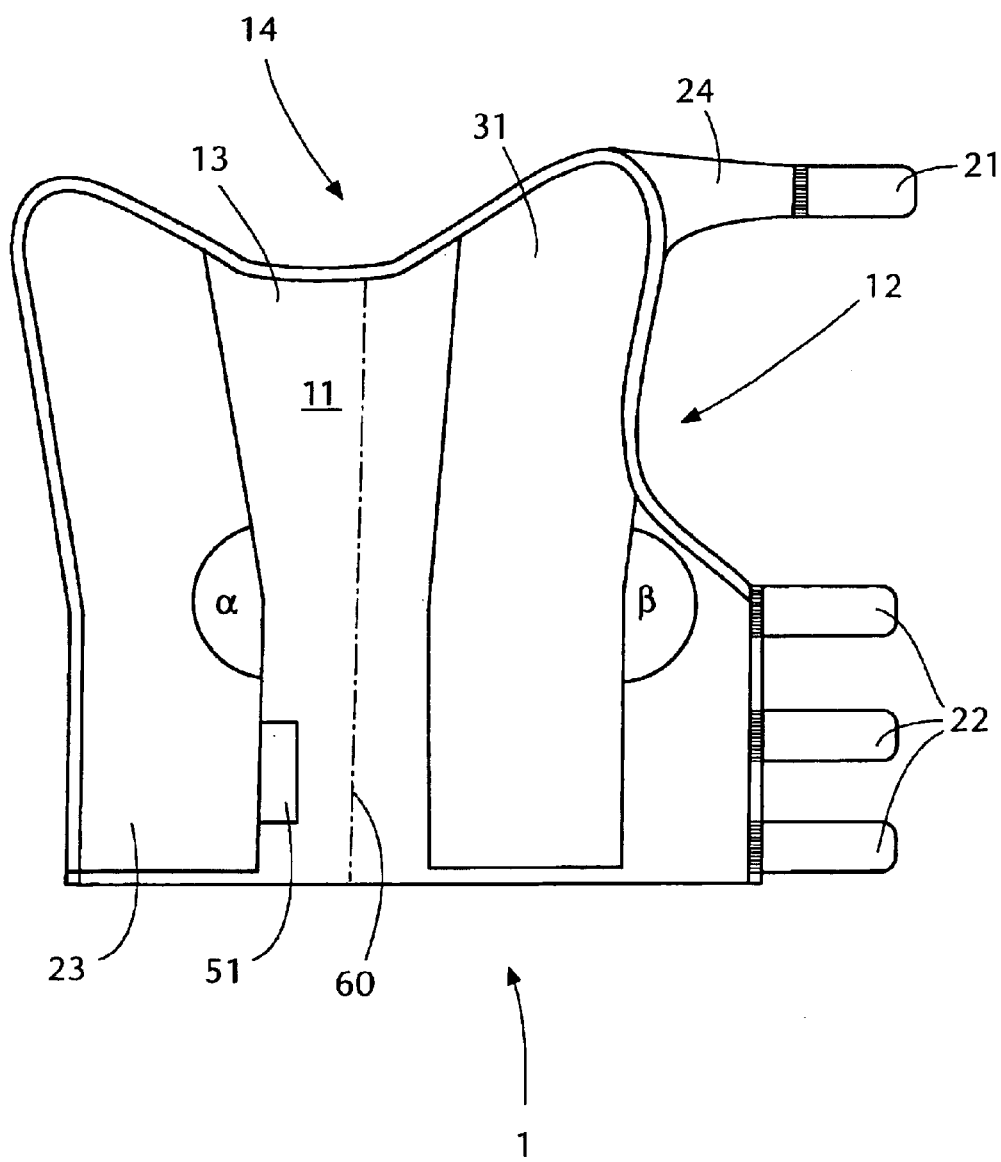
FIG. 1 shows the bandage according to the invention in the design for the right wrist.

In FIG. 1, the bandage (1) according to the invention in a preferred embodiment is shown in the state before it is applied. The bandage (1) is intended for the right wrist, and the one for the left wrist will have a mirror-image configuration.

The bandage (1) has a central, anatomically shaped section (11) which receives the wrist and the hand and which is formed from a single piece of transversely elastic material. The section (11) narrows in the proximal direction.

There is also a cutout (12) present on the medial edge, which cutout (12) serves to receive the right thumb when the bandage (1) is applied.

At the distal end of the section (11) there is a further cutout (14) for increasing the mobility of the fingers.

The section (11) has an elastic band (13) sewn round all its edges.

Moreover, a total of four straps (21, 22) are secured on the medial edge of the section (11), these straps (21, 22) serving to fix the bandage (1) on the hand and on the wrist, respectively. In addition, the straps (21, 22) have a velcro closure by means of which they are secured on a roughened surface (23), the roughened surface (23) being sewn onto the dorsal side of the bandage (1) in such a way that the centre axis of the surface (23) has an inwardly directed kink which encloses an angle α of 165°, the angle being indicated on one of the outer edges of the surface (23).

Although not shown here, a padding (24) is arranged underneath the strap (21) situated at the distal end of the medial edge, which padding (24) permits a more comfortable fit of the bandage (1).

A pocket (31) is sewn on the palmar side of the bandage (1) in such a way that the centre axis of the pocket (31) like the centre axis of the surface (23) encloses an angle β of 165°, this angle also being indicated on one of the outer edges of the pocket (31).

A splint (41) preferably made of aluminium is inserted into the pocket (31) so that, with the bandage (1) applied, the fixation and stabilization of the wrist are ensured.

Finally, a label, on which it is possible to indicate on which hand the bandage (1) is to be applied, is sewn onto the surface (23).

For applying the bandage (1), the latter is applied with the underside according to FIG. 1 on the inner surface of the patient's hand, so that the cutout (12) receives the thumb. The pocket (31) with the splint (41) extends from the inner surface of the hand over the wrist as far as the forearm. The section (11) is then placed round the hand and fixed firmly by means of the straps (21, 22).

Figure 2:
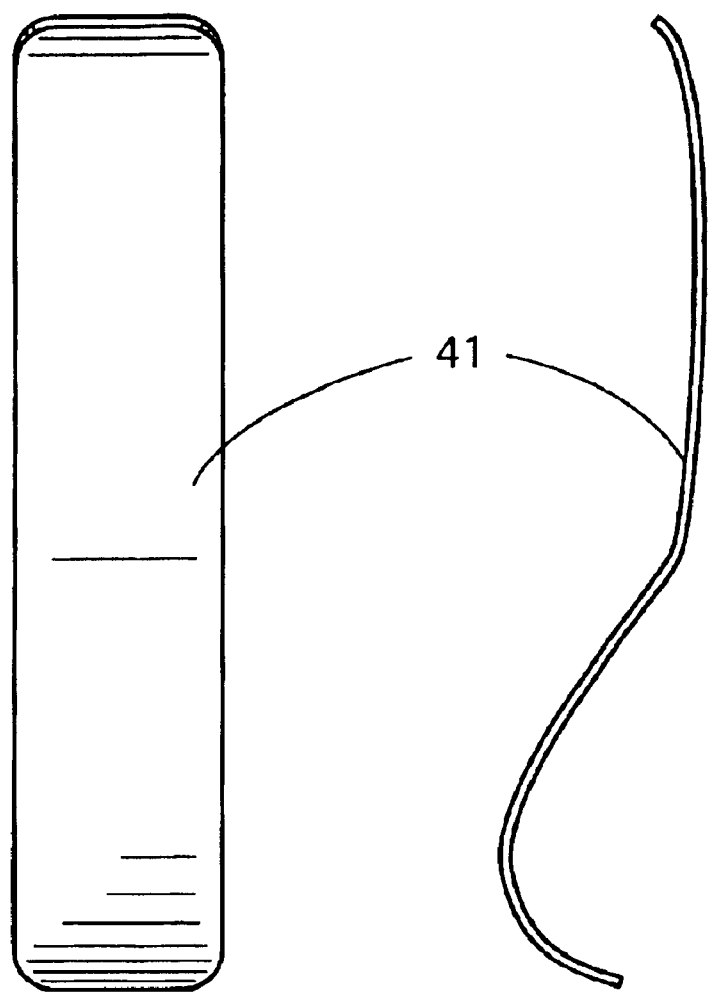
FIG. 2 shows the bandage splint which is inserted into the pocket of the bandage, namely in a plan view and in a side view.

FIG. 2 shows the splint (41) in a plan view and in a side view, illustrating the anatomically appropriate shape of the splint (41) for the inner surface of the hand, the splint (41) being made of aluminum and thus being largely inflexible.

Figure 3:
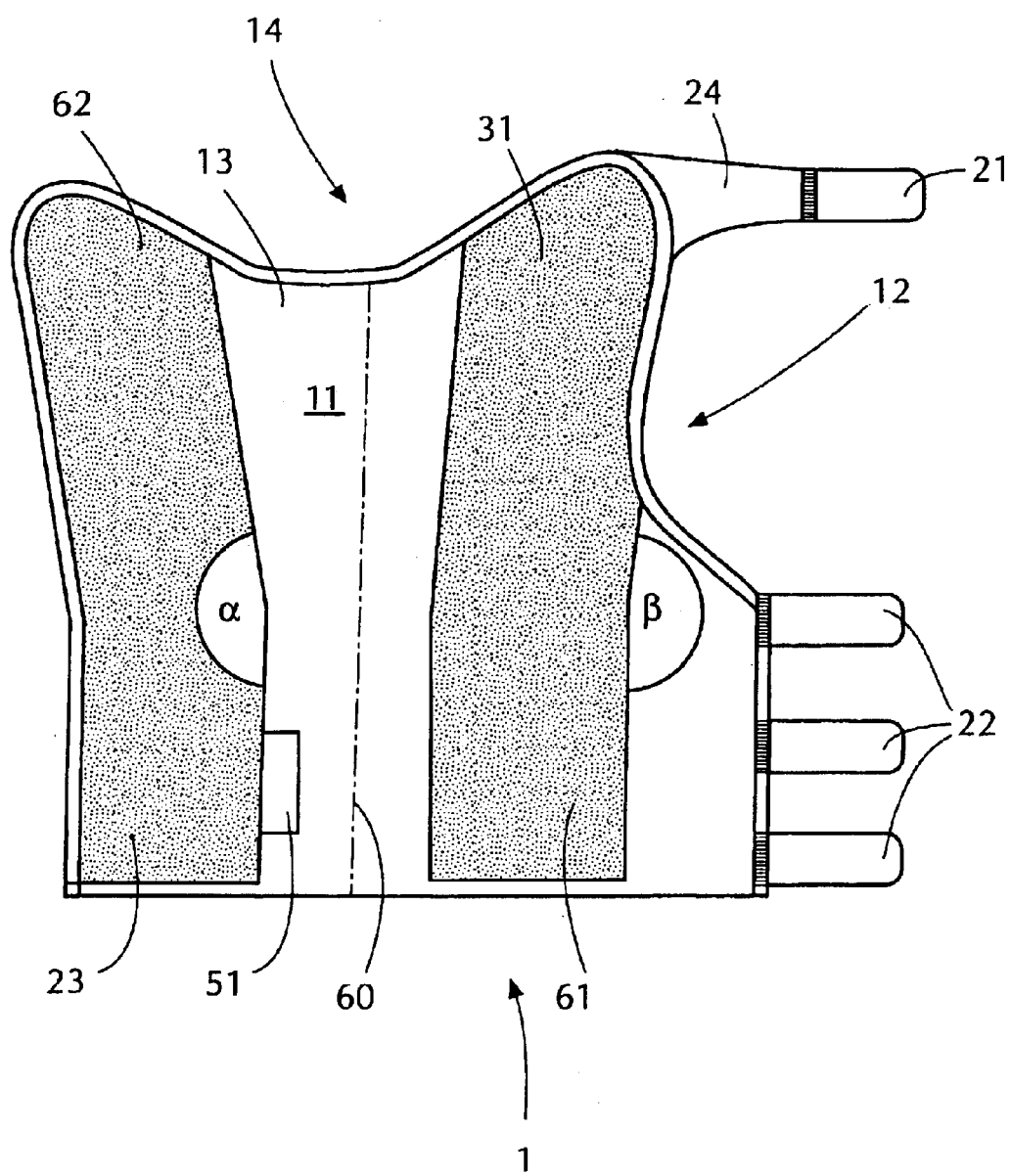
FIG. 3 shows the bandage according to an embodiment of the invention wherein the pocket secured on the palmar side of the bandage has a roughened surface and the roughened surface secured on the dorsal side of the bandage is designed as a pocket.

FIG. 3 shows a preferred embodiment of the bandage (1), the pocket (31) secured on the palmar side of the bandage, in particular sewn thereon, has a roughened surface (61) (as shown by the dotted area in element 31), and the roughened surface 23 (as shown by the dotted area in element 62) secured on the dorsal side of the bandage (1), in particular sewn thereon, is designed as a pocket (62). Thus, there are two preferably identical combinations of pocket/roughened surface present on the bandage. In this way, it is possible, with just a single design, to apply the bandage to either wrist, provided the splint has been inserted into the appropriate pocket.

What is claimed is:

1. A wrist bandage, comprising a single piece of flexible and elastic material, having a proximal edge, a distal edge, a medial edge, a palmer side and a dorsal side, said bandage being anatomically shaped and narrowing in the direction of the proximal edge; the medial edge having a cutout for receiving the thumb of a hand on a wrist to which the bandage is to be applied, with at least two straps being attached to the medial edge, which straps are removably attachable to the dorsal side of the bandage, the dorsal side being adapted to receive and secure said straps, said bandage having an elongated pocket secured to the palmer side thereof, which pocket is defined by two sides extending generally from the proximal edge to the distal edge, both of which have one kink or arch towards a central axis running from the proximal to the distal edge of the bandage and both of which are secured to the bandage and a generally rectangular substantially inflexible splint adapted to the anatomy of the inner surface of the hand is inserted into the pocket of the bandage.

2. Wrist bandage according to claim 1, wherein said pocket is kinked.

3. Bandage according to claim 2, wherein said pocket is kinked by an angle of 150° to 170°.

4. Bandage according to claim 1 or 2, wherein the straps are provided with a hook and loop closure which is secured on a roughened surface secured on the dorsal side of the bandage, the roughened surface extending from the distal edge of the bandage to the proximal edge and is kinked or arched towards the central axis running from the proximal to the distal edge of the bandage.

5. Bandage according to claim 1 or 2, wherein one strap of the bandage is secured at a distal end of the medial edge of the bandage with the strap having a palmar side, and the strap is provided with padding on the palmar side of the strap.

6. Bandage according to claim 1 or 2, wherein the bandage is made of a material which when the bandage is applied to a wrist is flexible in the medial and lateral direction of the wrist and substantially inflexible in the proximal and distal direction of the wrist.

7. Bandage according to claim 4, wherein the pocket secured on the palmar side of the bandage has a roughened surface, and the roughened surface secured on the dorsal side of the bandage is designed as a pocket.

* * * * *

UNITED STATES PATENT AND TRADEMARK OFFICE
CERTIFICATE OF CORRECTION

PATENT NO. : 6,730,053 B1
DATED : May 4, 2004
INVENTOR(S) : Bodenschatz et al.

It is certified that error appears in the above-identified patent and that said Letters Patent is hereby corrected as shown below:

<u>Column 3,</u>
Line 8, should read -- is possible without falling of the folds. --

<u>Column 4,</u>
Line 56, insert -- a -- between "with" and "padding"

Signed and Sealed this

Thirty-first Day of August, 2004

JON W. DUDAS
*Director of the United States Patent and Trademark Office*